United States Patent
Girouard et al.

(10) Patent No.: US 8,275,456 B2
(45) Date of Patent: Sep. 25, 2012

(54) IMPLANTABLE DEVICE FOR DELIVERING CARDIAC DRUG THERAPY

(75) Inventors: Steven D. Girouard, Woodbury, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 770 days.

(21) Appl. No.: 11/425,263

(22) Filed: Jun. 20, 2006

(65) Prior Publication Data
US 2006/0247686 A1 Nov. 2, 2006

Related U.S. Application Data

(63) Continuation of application No. 10/293,907, filed on Nov. 12, 2002, now Pat. No. 7,072,711.

(51) Int. Cl.
*A61N 1/00* (2006.01)
*A61N 5/04* (2006.01)
(52) U.S. Cl. ............... 607/3; 600/509; 600/517
(58) Field of Classification Search .............. 600/509, 600/517; 607/3
See application file for complete search history.

(56) References Cited

U.S. PATENT DOCUMENTS

| | | |
|---|---|---|
| 3,692,027 A | 9/1972 | Ellinwood, Jr. |
| 4,003,379 A | 1/1977 | Ellinwood, Jr. |
| 4,146,029 A | 3/1979 | Ellinwood, Jr. |
| 4,281,664 A | 8/1981 | Duggan |
| 4,299,220 A | 11/1981 | Dorman |
| 4,544,371 A | 10/1985 | Dormandy, Jr. et al. |
| 4,556,063 A | 12/1985 | Thompson et al. |
| 4,561,443 A | 12/1985 | Hogrefe et al. |
| 4,674,518 A | 6/1987 | Salo |
| 4,686,987 A | 8/1987 | Salo et al. |
| 4,871,351 A | 10/1989 | Feingold |
| 4,897,987 A | 2/1990 | Spalla |
| 4,924,875 A * | 5/1990 | Chamoun ............. 600/509 |
| 4,944,299 A | 7/1990 | Silvian |
| 4,987,897 A | 1/1991 | Funke |
| 5,014,698 A | 5/1991 | Cohen |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,087,243 A | 2/1992 | Avitall |

(Continued)

FOREIGN PATENT DOCUMENTS

EP 0054138 6/1982

(Continued)

OTHER PUBLICATIONS

"PCT International Search Report", from counterpart International Application No. PCT/US 03/36364, dated Apr. 16, 2004, 5 pages.

(Continued)

*Primary Examiner* — Nicole F Lavert
(74) *Attorney, Agent, or Firm* — Schwegman Lundberg & Woessner, P.A.

(57) ABSTRACT

An implantable medical device in which an electrogram is recorded and analyzed in order to detect changes indicative of cardiac ischemia. Cardiac ischemia may be detected by recording an electrogram from a sensing channel of the device and comparing the recorded electrogram with a reference electrogram. If cardiac ischemia is detected, a cardiac drug such as a thrombolytic agent is delivered.

16 Claims, 5 Drawing Sheets

U.S. PATENT DOCUMENTS

| | | | |
|---|---|---|---|
| 5,113,869 A | 5/1992 | Nappholz et al. | |
| 5,127,404 A | 7/1992 | Wyborny et al. | |
| 5,137,019 A | 8/1992 | Pederson et al. | |
| 5,181,519 A | 1/1993 | Bible | |
| 5,184,614 A | 2/1993 | Collins et al. | |
| 5,190,035 A | 3/1993 | Salo et al. | |
| 5,199,428 A | 4/1993 | Obel et al. | |
| 5,220,917 A | 6/1993 | Cammilli et al. | |
| 5,226,424 A | 7/1993 | Bible | |
| 5,265,617 A | 11/1993 | Verrier et al. | |
| 5,269,301 A | 12/1993 | Cohen | |
| 5,284,136 A | 2/1994 | Hauck et al. | |
| 5,305,745 A | 4/1994 | Zacouto | |
| 5,334,222 A | 8/1994 | Salo et al. | |
| 5,342,408 A | 8/1994 | deCoriolis et al. | |
| 5,353,800 A | 10/1994 | Pohndorf et al. | |
| 5,368,028 A | 11/1994 | Palti | |
| 5,391,190 A | 2/1995 | Pederson et al. | |
| 5,404,877 A | 4/1995 | Nolan et al. | |
| 5,416,695 A | 5/1995 | Stutman et al. | |
| 5,417,717 A | 5/1995 | Salo et al. | |
| 5,456,692 A | 10/1995 | Smith, Jr. et al. | |
| 5,460,605 A | 10/1995 | Tuttle et al. | |
| 5,487,752 A | 1/1996 | Salo et al. | |
| 5,496,360 A | 3/1996 | Hoffmann et al. | |
| 5,499,971 A | 3/1996 | Shapland et al. | |
| 5,540,728 A | 7/1996 | Shelton et al. | |
| 5,545,186 A | 8/1996 | Olson et al. | |
| 5,551,953 A | 9/1996 | Lattin et al. | |
| 5,556,421 A | 9/1996 | Prutchi et al. | |
| 5,562,713 A | 10/1996 | Silvian | |
| 5,579,876 A | 12/1996 | Adrian et al. | |
| 5,584,868 A | 12/1996 | Salo et al. | |
| 5,586,556 A | 12/1996 | Spivey et al. | |
| 5,591,215 A | 1/1997 | Greenhut et al. | |
| 5,603,331 A | 2/1997 | Heemels et al. | |
| 5,607,418 A | 3/1997 | Arzbaecher | |
| 5,607,463 A | 3/1997 | Schwartz et al. | |
| 5,632,766 A | 5/1997 | Hsu et al. | |
| 5,634,899 A | 6/1997 | Shapland et al. | |
| 5,662,689 A | 9/1997 | Elsberry et al. | |
| 5,683,424 A | 11/1997 | Brown et al. | |
| 5,690,682 A | 11/1997 | Buscemi et al. | |
| 5,693,075 A | 12/1997 | Plicchi et al. | |
| 5,703,125 A | 12/1997 | Bovy et al. | |
| 5,720,770 A | 2/1998 | Nappholz et al. | |
| 5,730,125 A | 3/1998 | Prutchi et al. | |
| 5,749,900 A | 5/1998 | Schroeppel et al. | |
| 5,800,498 A | 9/1998 | Obino et al. | |
| 5,814,089 A | 9/1998 | Stokes et al. | |
| 5,817,131 A | 10/1998 | Elsberry et al. | |
| 5,833,603 A | 11/1998 | Kovacs et al. | |
| 5,836,935 A | 11/1998 | Ashton et al. | |
| 5,893,881 A | 4/1999 | Elsberry et al. | |
| 5,899,928 A | 5/1999 | Sholder et al. | |
| 5,919,210 A | 7/1999 | Lurie et al. | |
| 5,921,940 A | 7/1999 | Verrier et al. | |
| 5,925,066 A | 7/1999 | Kroll et al. | |
| 5,944,710 A | 8/1999 | Dev et al. | |
| 5,949,659 A | 9/1999 | Lesche | |
| 5,967,986 A | 10/1999 | Cimochowski et al. | |
| 5,991,668 A | 11/1999 | Leinders et al. | |
| 6,016,443 A * | 1/2000 | Ekwall et al. | 600/519 |
| 6,016,447 A | 1/2000 | Juran et al. | |
| 6,016,448 A | 1/2000 | Busacker et al. | |
| 6,021,350 A | 2/2000 | Mathson | |
| 6,022,322 A | 2/2000 | Prutchi | |
| 6,104,949 A | 8/2000 | Pitts Crick et al. | |
| 6,112,116 A * | 8/2000 | Fischell et al. | 600/517 |
| 6,112,117 A | 8/2000 | KenKnight et al. | |
| 6,115,636 A | 9/2000 | Ryan | |
| 6,128,526 A | 10/2000 | Stadler et al. | |
| 6,140,740 A | 10/2000 | Porat et al. | |
| 6,141,588 A | 10/2000 | Cox et al. | |
| 6,154,675 A | 11/2000 | Juran et al. | |
| 6,155,267 A | 12/2000 | Nelson | |
| 6,161,042 A | 12/2000 | Hartley et al. | |
| 6,168,801 B1 | 1/2001 | Heil, Jr. et al. | |
| 6,198,394 B1 | 3/2001 | Jacobsen et al. | |
| 6,200,265 B1 | 3/2001 | Walsh et al. | |
| 6,203,495 B1 | 3/2001 | Bardy | |
| 6,206,914 B1 | 3/2001 | Soykan et al. | |
| 6,213,942 B1 | 4/2001 | Flach et al. | |
| 6,221,011 B1 | 4/2001 | Bardy | |
| 6,224,553 B1 | 5/2001 | Nevo | |
| 6,231,516 B1 | 5/2001 | Keilman et al. | |
| 6,237,398 B1 | 5/2001 | Porat et al. | |
| 6,251,125 B1 | 6/2001 | KenKnight et al. | |
| 6,254,573 B1 | 7/2001 | Haim et al. | |
| 6,256,233 B1 | 7/2001 | Glass | |
| 6,256,538 B1 | 7/2001 | Ekwall | |
| 6,261,230 B1 | 7/2001 | Bardy | |
| 6,264,606 B1 * | 7/2001 | Ekwall et al. | 600/300 |
| 6,266,554 B1 | 7/2001 | Hsu et al. | |
| 6,270,457 B1 | 8/2001 | Bardy | |
| 6,272,377 B1 | 8/2001 | Sweeney et al. | |
| 6,272,379 B1 | 8/2001 | Fischell et al. | |
| 6,275,727 B1 | 8/2001 | Hopper et al. | |
| 6,277,072 B1 | 8/2001 | Bardy | |
| 6,277,078 B1 | 8/2001 | Porat et al. | |
| 6,278,894 B1 | 8/2001 | Salo et al. | |
| 6,280,380 B1 | 8/2001 | Bardy | |
| 6,280,409 B1 | 8/2001 | Stone et al. | |
| 6,298,272 B1 | 10/2001 | Peterfeso et al. | |
| 6,309,370 B1 | 10/2001 | Haim et al. | |
| 6,312,378 B1 | 11/2001 | Bardy | |
| 6,331,160 B1 | 12/2001 | Bardy | |
| 6,336,903 B1 | 1/2002 | Bardy | |
| 6,339,720 B1 | 1/2002 | Anzellini et al. | |
| 6,358,202 B1 | 3/2002 | Arent | |
| 6,358,203 B2 | 3/2002 | Bardy | |
| 6,361,522 B1 | 3/2002 | Scheiner et al. | |
| 6,361,780 B1 | 3/2002 | Ley et al. | |
| 6,368,284 B1 | 4/2002 | Bardy | |
| 6,370,424 B1 | 4/2002 | Prutchi | |
| 6,398,728 B1 | 6/2002 | Bardy | |
| 6,411,840 B1 | 6/2002 | Bardy | |
| 6,424,847 B1 | 7/2002 | Mastrototaro et al. | |
| 6,438,408 B1 | 8/2002 | Mulligan et al. | |
| 6,438,419 B1 | 8/2002 | Callaway et al. | |
| 6,440,066 B1 | 8/2002 | Bardy | |
| 6,442,413 B1 | 8/2002 | Silver | |
| 6,443,949 B2 | 9/2002 | Altman | |
| 6,453,195 B1 | 9/2002 | Thompson | |
| 6,459,917 B1 | 10/2002 | Gowda et al. | |
| 6,459,929 B1 | 10/2002 | Hopper et al. | |
| 6,468,263 B1 | 10/2002 | Fischell et al. | |
| 6,478,737 B2 | 11/2002 | Bardy | |
| 6,501,983 B1 | 12/2002 | Natarajan et al. | |
| 6,507,753 B1 | 1/2003 | Xue et al. | |
| 6,511,477 B2 | 1/2003 | Altman et al. | |
| 6,518,245 B1 | 2/2003 | Anderson et al. | |
| 6,532,381 B2 | 3/2003 | Bayer et al. | |
| 6,539,256 B1 | 3/2003 | KenKnight et al. | |
| 6,609,023 B1 | 8/2003 | Fischell et al. | |
| 6,628,985 B2 | 9/2003 | Sweeney et al. | |
| 6,645,145 B1 | 11/2003 | Dreschel et al. | |
| 6,689,117 B2 | 2/2004 | Sweeney et al. | |
| 6,824,561 B2 | 11/2004 | Soykan et al. | |
| 6,865,420 B1 | 3/2005 | Kroll | |
| 6,882,883 B2 | 4/2005 | Condie et al. | |
| 6,985,771 B2 | 1/2006 | Fischell et al. | |
| 7,010,345 B2 | 3/2006 | Hill et al. | |
| 7,066,891 B2 | 6/2006 | Stadler et al. | |
| 7,072,711 B2 * | 7/2006 | Girouard et al. | 607/3 |
| 7,254,440 B1 | 8/2007 | Kroll | |
| 7,272,436 B2 | 9/2007 | Gill et al. | |
| 7,297,114 B2 | 11/2007 | Gill et al. | |
| 7,340,303 B2 | 3/2008 | Zhu | |
| 7,369,892 B2 | 5/2008 | Ferek-Petric | |
| 7,512,438 B2 | 3/2009 | Fischell et al. | |
| 7,524,287 B2 | 4/2009 | Bharmi | |
| 7,558,623 B2 | 7/2009 | Fischell et al. | |
| 7,567,841 B2 | 7/2009 | Chan | |
| 7,577,478 B1 | 8/2009 | Kroll et al. | |
| 2001/0000802 A1 | 5/2001 | Soykan et al. | |
| 2002/0013612 A1 * | 1/2002 | Whitehurst | 607/45 |

| | | |
|---|---|---|
| 2002/0026228 A1 | 2/2002 | Schauerte |
| 2002/0091415 A1* | 7/2002 | Lovett et al. .................. 607/14 |
| 2002/0099328 A1 | 7/2002 | Scheiner et al. |
| 2002/0120306 A1 | 8/2002 | Zhu et al. |
| 2003/0004403 A1 | 1/2003 | Drinan et al. |
| 2003/0023175 A1 | 1/2003 | Arzbaecher et al. |
| 2003/0045805 A1 | 3/2003 | Sheldon et al. |
| 2003/0060854 A1 | 3/2003 | Zhu |
| 2003/0069606 A1 | 4/2003 | Girouard et al. |
| 2003/0149354 A1 | 8/2003 | Bakharev |
| 2003/0149423 A1 | 8/2003 | Fischell |
| 2003/0158584 A1 | 8/2003 | Cates |
| 2003/0191402 A1 | 10/2003 | Arzbaecher et al. |
| 2003/0233132 A1 | 12/2003 | Pastore et al. |
| 2004/0002739 A1 | 1/2004 | Cates et al. |
| 2004/0049235 A1 | 3/2004 | Deno et al. |
| 2004/0059238 A1 | 3/2004 | Fischell et al. |
| 2004/0059391 A1 | 3/2004 | Sweeney et al. |
| 2004/0073262 A1 | 4/2004 | Lovett |
| 2004/0093034 A1 | 5/2004 | Girouard et al. |
| 2005/0043639 A1 | 2/2005 | Fischell |
| 2005/0043675 A1 | 2/2005 | Pastore et al. |
| 2005/0065445 A1 | 3/2005 | Arzbaecher et al. |
| 2005/0075673 A1 | 4/2005 | Warkentin et al. |
| 2005/0085736 A1 | 4/2005 | Ambrose et al. |
| 2005/0137483 A1 | 6/2005 | Fischell et al. |
| 2005/0256417 A1 | 11/2005 | Fischell et al. |
| 2006/0253044 A1 | 11/2006 | Zhang |
| 2006/0265020 A1 | 11/2006 | Fischell et al. |
| 2007/0093720 A1 | 4/2007 | Fischell et al. |
| 2007/0208263 A1 | 9/2007 | John et al. |
| 2007/0249944 A1 | 10/2007 | Fischell et al. |
| 2007/0249947 A1 | 10/2007 | Fischell et al. |
| 2007/0276453 A1 | 11/2007 | Hill et al. |
| 2007/0293775 A1 | 12/2007 | Fischell et al. |
| 2007/0293778 A1 | 12/2007 | Fischell et al. |
| 2008/0058660 A1 | 3/2008 | Fischell et al. |
| 2008/0064973 A1 | 3/2008 | Fischell et al. |
| 2008/0139954 A1 | 6/2008 | Day et al. |
| 2008/0183091 A1 | 7/2008 | Fischell et al. |
| 2008/0188762 A1 | 8/2008 | John et al. |
| 2008/0188763 A1 | 8/2008 | John et al. |
| 2009/0048528 A1 | 2/2009 | Hopenfeld et al. |
| 2009/0076403 A1 | 3/2009 | Hopenfeld |
| 2009/0082682 A1 | 3/2009 | Fischell et al. |
| 2009/0171228 A1 | 7/2009 | Fischell et al. |
| 2009/0192397 A1 | 7/2009 | Fischell et al. |
| 2009/0216141 A1 | 8/2009 | Fischell et al. |
| 2009/0259268 A1 | 10/2009 | Chan |

FOREIGN PATENT DOCUMENTS

| | | |
|---|---|---|
| EP | 0467695 A2 | 1/1992 |
| EP | 0545628 A2 | 6/1993 |
| EP | 1050265 | 11/2000 |
| WO | WO-97/33513 | 9/1997 |
| WO | WO-9834537 A1 | 8/1998 |
| WO | WO-0007497 A1 | 2/2000 |

OTHER PUBLICATIONS

Arnaud, Claire, et al., "iNOS is a mediator of the heat stress-induced preconditioning against myocardial infarction in vivo in the rat", *Cardiovascular Research*, 58, (2003), 118-125.

Bralet, J, et al., "Vasopeptidase inhibitors: an emerging class of cardiovascular drugs", *Trends Pharmacol Sci.*, 22(3), (Mar. 2001), 106-9.

Brunner, Friedrich, "Attenuation of myocardial ischemia/reperrusion injury in mice with myocyte-specific overexpression of endothelial nitric oxide synthase", *Cardiovascular Research*, 57, (2003), 55-62.

Burns, Brent E., "Fabrication Technology for a Chronic In-Vivo Pressure Sensor", *1984 International Electron Devices Meeting Technical Digest*, (1984), 210-212.

Carr, William N., "Integrated Pressure Sensor With Remote Power Source and Remote Readout", *The 8th International Conference on Solid-State Sensors and Actuators and Eurosensors IX. Digest of Technical Papers*, Stockholm, Sweden. (Jun. 25-29, 1995), 624-627.

Chau, Hin-Leung, "An Ultraminiature Solid-State Pressure Sensor for a Cardiovascular Catheter", *IEEE Transactions on Electron Devices*, (Dec. 1988), 2355-2362.

Colonna, P, et al., "Myocardial infarction and left ventricular remodeling: results of the CEDIM trial. Carnitine Ecocardiografia Digitalizzata Infarto Mio", *Am Heart J.*, 139(2 Pt 3), (Feb. 2000), S124-30.

Ferdinandy, Peter, et al., "Nitric oxide, superoxide, and peroxynitrite in myocardial ischaemia-reperfusion injury and preconditioning", *British Journal of Pharmacology*, 138(4), (2003), 532-543.

Flogel, Ulrich, "Myoglobin: A scanvenger of Bioactive NO", *PNAS*, 98(2), (Jan. 16, 2001), 735-740.

Gewaltig, Michael T., "Vasoprotection by nitric oxide: mechanisms and therapeutic potential", *Cardiovascular Research*, 55, (Feb. 14, 2002), 250-260.

Hada, Yoshiyuki, et al., "Pulsus alternans determined by biventricular simultaneous systolic time intervals", *Circulation*, 65(3). (Mar. 1982), 617-26.

Lee, Y. C., et al., "Pulsus alternans in patients with congestive cardiomyopathy", *Circulation*, 65(7), (Jun. 1982), 1533-4.

Lehman, J, et al., "Gene regulatory mechanisms governing energy metabolism during cardiac hypertrophic growth", *Heart Fail Rev.*, (Apr. 2000), 175-85.

Levin, L, "Researchers present findings at European cardiology conference", *Advisory Board Daily Briefing, 8. Clinical Outlook*, (Sep. 2002), 8 pages [see pp. 5,6].

Li, Qianghong, "Gene Therapy With Inducible Nitric Oxide Synthase Protects Against Myocardial Infarction via a Cyclooxygenase-2-Dependent Mechanism", *Circulation Research*, 92, (2003), 741-748.

Lopaschuk, G, "Metabolic abnormalities in the diabetic heart", *Heart Fail Rev.*, 7(2), (Apr. 2002), 149-59.

Luepker, R., "Transthoracic Electrical Impedance: Quantitative Evaluation of a Non-Invasive Measure of Thoracic Fluid Volume", *American Heart Journal*, 85(1), (Jan. 1973), 83-93.

Min, Mart, "Electrical Impedance and Cardiac Monitoring-Technology, Potential and Applications", *International Journal of Bioelectromagnetism*, 5(1), (2003), 53-56.

Ostadal, Petr, et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003), 45-50.

Paolocci, Nazareno, et al., "Positive inotropic and lusitropic effects of HNO/NO- in failing hearts: Independence from beta-adrenergic signaling", *Proceedings of the National Academy of Sciences USA*, 100(9), (Apr. 29, 2003), 5537-5542.

Pastore, Joseph M., "Drug Delivery System and Method Employing External Drug Delivery Device in Conjunction With Computer Network", U.S. Appl. No. 10/742,574, filed Dec. 19, 2003, 36 pages.

Pastore, Joseph M., "Method and Apparatus for Modulating Cellular Metabolism During Post-Ischemia or Heart Failure", U.S. Appl. No. 10/645,823, filed Aug. 21, 2003, 46 pages.

Rizos, I, "Three-year survival of patients with heart failure caused by dilated cardiomyopathy and L-carnitine administration", *Am Heart J.*, 139(2 Pt3), (Feb. 2000), Am Heart J.

Sabbah, H, et al., "Partial fatty acid oxidation inhibitors: a potentially new class of drugs for heart failure", *Eur J Heart Fail.*, 4(1) (Jan. 2002), 3-6.

Salloum, Fadi, "Sildenafil Induces Delayed Preconditioning Through Inducible Nitric Oxide Synthase-Dependent Pathway in Mouse Heart", *Circulation Research*, 92, (Apr. 4, 2003), 595-597.

Schaefer, Saul, et al., "Clinical and hemodynamic characteristics of patients with inducible pulsus alternans", *American Heart Journal*, vol. 115, No. 6, (Jun. 1988), 1251-7.

Smith, Damon, et al., "Influence of the Aortic Component of the Second Heart Sound on Left Ventricular Maximal Negative dP/dt in the Dog", *Am. J. Cardiol.*, 55: 205, (1985), 205-209.

Spiegel, Egbert, "A CMOS Sensor and Signal Conversion Chip for Monitoring Arterial Blood Pressure and Temperature", *IEEE International Solid-State Circuits Conference.*, (Feb. 20, 1992), 126-127.

Stanley, W, et al., "Energy metabolism in the normal and failing heart: potential for therapeutic interventions", *Heart Fail Rev.*, (Apr. 2002), 115-30.

Stanley, W, "Partial fatty acid oxidation inhibitors for stable angina", *Expert Opin Investig Drugs*, 11(5), (May 2002),615-29.

Suematsu, Yoshihiro, et al., "L-Arginine given after ischaemic preconditioning can enhance cardioprotection in isolated rat hearts", *European Journal of Cardio-thoracic Surgery*, 19, (2001),873-879.

Sweeney, Robert J., et al., "Drug Delivery System for Implantable Medical Device", U.S. Appl. No. 10/743,507, filed Dec. 22, 2003, 17.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolff, A, et al., "Metabolic approaches to the treatment of ischemic heart disease: the clinicians' perspective", *Heart Fail Rev.*, (Apr. 2002),187-203.

Wolfrum, Sebastian, et al., "Acute Reduction of Myocardial Infarct Size by a Hydroxymethyl Glutaryl Coenzyme a Reductase Inhibitor is Mediated by Endothelial Nitric Oxide Synthase", *J. Cardiovas Pharmacol*, vol. 41, No. 3, (Mar. 2003),474-480.

Wunderlich, Carsten, "Acute Inhibition of Myoglobin Imparis Contractility and Energy State of iNOS-Overexpressing Hearts", *Circulation Research*, 92, (2003),1352-1358.

Wynn, R, "Cardiovascular drugs and dental considerations", *Cardiovascular drugs and dental considerations, J Calif Dent Assoc.*, 28(7), (Jul. 2000),9-26.

Ziaie, Babak, "A Single-Channel Implantable Microstimulator for Functional Neuromuscular Stimulation", *IEEE Transactions on Biomedical Engineering*, 44, (Oct. 1997),909-920.

"U.S. Appl. No. 10/742,574, Response filed Apr. 15, 2010 to Final Office Action dated Jan. 15, 2010", 12 pgs.

"U.S. Appl. No. 10/742,574, Advisory Action mailed May 3, 2010", 3 pgs.

"U.S. Appl. No. 11/998,969 Non-Final Office Action mailed Jul. 12, 2010", 12 pgs.

"U.S. Appl. No. 11/998,969, Response file Apr. 26, 2010 to Restriction Requirement maield Mar. 25, 2010", 10 pgs.

"U.S. Appl. No. 11/998,969, Response filed Oct. 12, 2010 to Non Final Office Action maied Jul. 12, 2010", 10 pgs.

* cited by examiner

IMPLANTABLE DEVICE FOR DELIVERING CARDIAC DRUG THERAPY

CROSS-REFERENCE TO RELATED APPLICATION(S)

This application is a continuation of U.S. application Ser. No. 10/293,907, filed on Nov. 12, 2002, now U.S. Pat. No. 7,072,711, which is incorporated herein by reference.

This application is related to U.S. application Ser. No. 09/962,852, filed on Sep. 25, 2001, now U.S. Pat. No. 7,340,303, the specification of which is herein incorporated by reference.

FIELD OF THE INVENTION

This invention pertains to implantable devices for detecting and treating cardiac disorders.

BACKGROUND

A major cause of cardiac death is acute coronary occlusion causing myocardial ischemia which results in a myocardial infarction or precipitates a lethal arrhythmia. Most patients currently treated for ventricular arrhythmias with an implantable cardioverter-defibrillator (ICD) have concurrent coronary artery disease, making them highly susceptible to ischemic events that may result in death. Although presently available ICDs can be beneficial during an acute ischemic episode by terminating any resulting arrhythmias with electrical stimulation, they do nothing to directly treat the occlusion. Present medical treatments are successful in managing acute coronary occlusion by dissolving the thrombus with chemical agents and preventing its reformation. Such treatments are generally performed only in an emergency-room setting, however, and in certain circumstances, only immediate relief from the ischemia can save the patient's life.

SUMMARY OF THE INVENTION

The present invention relates to an implantable cardiac device with the capability of detecting ischemic events and delivering cardiac drug therapy in response thereto. Such a device may be configured to also operate as a cardiac pacemaker and/or ICD. In order to detect ischemic events, the sensing channels of the device record an electrogram that is analyzed to detect changes indicative of cardiac ischemia. Upon detection of an ischemic event, the device is configured to automatically deliver a cardiac drug such as a thrombolytic agent. The recorded and analyzed electrogram may represent either intrinsic cardiac activity or an evoked response to a pace where the device is also configured to deliver cardiac pacing. In the latter case, the electrogram is recorded from an evoked response sensing channel that senses the depolarization of the myocardium brought about by the delivery of a pacing stimulus, where the evoked response sensing channel may be the sensing/pacing channel used for delivering the stimulus or another sensing channel, such as one dedicated for that purpose.

In order to detect an ischemic change, the electrogram is compared with a reference electrogram to ascertain if a morphological marker of ischemia is present, such as increased current of injury. The comparison may involve, for example, cross-correlating the recorded and reference electrograms or comparing ST segment amplitudes, slopes, or integrations with reference values. Any of these means also allows the degree of ischemia to be quantified to determine if drug therapy is warranted.

DETAILED DESCRIPTION

As noted above, chemical agents are available today that can successfully treat cardiac ischemia due to coronary occlusion by dissolving the thrombus or blood clot. Such agents include tissue plasminogen activators (tPA), streptokinase, and similar drugs. Agents are also available that do not directly dissolve existing blood clots but act to prevent further clotting. These agents include low and high molecular weight heparin and anti-platelet drugs such as aspirin and similar drugs. Other drugs may also be administered to treat the effects of the ischemia such as anti-arrhythmic agents, beta-blockers, nitrates, and angiogenic agents. Because time is often of the essence in treating cardiac ischemic episodes, it would be beneficial for an implantable device to have the capability of automatically delivering cardiac drugs that would either resolve the situation or stabilize the patient enough so that further medical treatment could be obtained. Administration of cardiac drugs is not without risk, however, especially thrombolytic agents or drugs that otherwise inhibit hemostasis. Nevertheless, certain selected patients could benefit from automatic drug administration if a condition warranting such administration could be detected with sufficient specificity. The present invention relates to an implantable medical device that is configurable to automatically deliver one or more cardiac drugs upon detection of cardiac ischemia. The methods for detection of such ischemia detailed below also allow the detection to be quantified so that the extent of ischemia can be ascertained. The device may then be programmed by a clinician to deliver drugs only when ischemia of a specified degree is present.

1. Exemplary Hardware Platform

Figure 1A:
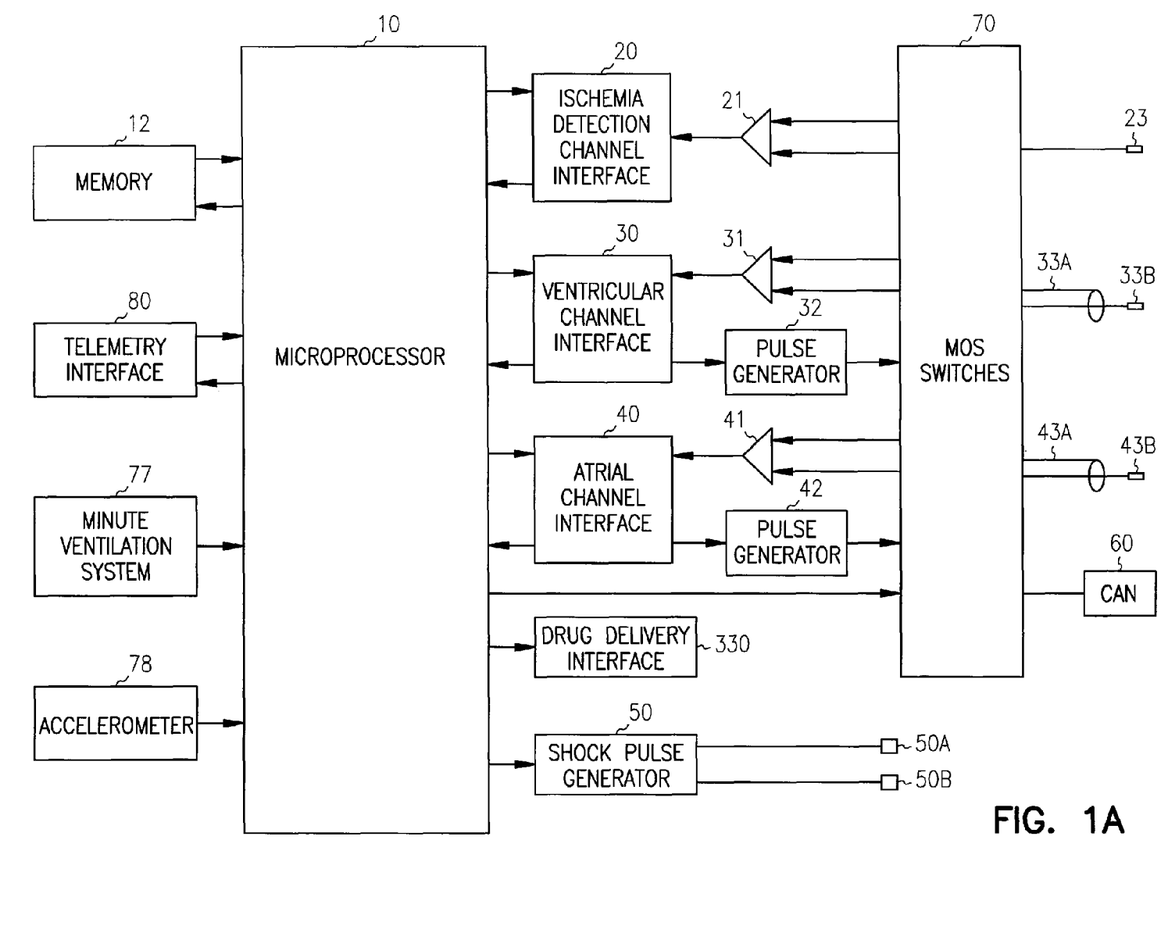
FIG. 1A is a block diagram of an exemplary cardiac device with drug delivery capability.

Cardiac rhythm management devices such as pacemakers and ICDs are typically implanted subcutaneously in a patient's chest and have leads threaded intravenously into the heart to connect the device to electrodes used for sensing, pacing, or delivery of defibrillation shocks. A programmable electronic controller causes the pacing pulses to be output in response to lapsed time intervals and sensed electrical activity (i.e., intrinsic heart beats not as a result of a pacing pulse) or defibrillation shocks to be delivered when an arrhythmia is detected. The present invention may be incorporated into a pacemaker or ICD or a dedicated device that is similarly implanted which is equipped with cardiac leads for sensing cardiac activity in order to detect ischemia. For illustrative purposes, however, a block diagram of an implantable device with dual-chamber pacing (i.e., the atria and ventricles) and cardioversion/defibrillation capability is shown in FIG. 1A. The controller of the device is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the terms "circuitry" or "programmed controller" should be taken to encompass either custom circuitry (i.e., dedicated hardware) or processor-executable instructions contained in a memory along with associated circuit elements.

The device has an atrial sensing/pacing channel comprising ring electrode 43a, tip electrode 43b, sense amplifier 41, pulse generator 42, and an atrial channel interface 40 which communicates bidirectionally with a port of microprocessor 10. The device also has a ventricular sensing/pacing channel that includes ring electrodes 33a, tip electrodes 33b, sense amplifier 31, pulse generator 32, and a ventricular channel interface 30. For each channel, the electrodes are connected to the pacemaker by a lead and used for both sensing and pacing. The channel interfaces may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A MOS switching network 70 controlled by the microprocessor is used to switch the electrodes from the input of a sense amplifier to the output of a pulse generator. A minute ventilation sensor 77 and an accelerometer 78 are provided in order to sense the patient's minute ventilation and body activity, respectively. The device may use the sensed minute ventilation and/or the accelerometer signal to adjust the rate at which the pacing pulses are delivered to the heart in the absence of a faster intrinsic rhythm, sometimes called rate-adaptive pacing. A shock pulse generator 50 with shock leads 50a and 50b for delivering cardioversion/defibrillation shocks is also interfaced to the controller.

The device also has an ischemia detection sensing channel that comprises an ischemia detection channel interface 20 and a sense amplifier 21 that has its differential inputs connected to a unipolar electrode 23 and to the device housing or can 60 through the switching network 70. The ischemia detection channel may be used to record an electrogram in order to detect ischemia as described below, where the electrogram may represent either intrinsic cardiac activity or an evoked response to a pacing pulse. When configured to sense evoked responses, the channel can also be used to verify that a pacing pulse has achieved capture of the heart and caused a contraction.

The microprocessor 10 controls the overall operation of the device in accordance with programmed instructions stored in memory. The sensing circuitry of the device generates atrial and ventricular sense signals when electrogram signals sensed by the electrodes exceed a specified threshold. The controller then interprets sense signals from the sensing channels and controls the delivery of paces in accordance with a programmed pacing mode. The sense signals from any of the sensing channels of the device can also be digitized and recorded by the controller to constitute an electrogram that can be analyzed to determine if ischemia is present, as well as either transmitted via a telemetry link 80 to an external programmer or stored for later transmission. A drug delivery interface 330 enables the controller to actuate a drug delivery apparatus in order to deliver a cardiac drug to the patient when an ischemic event is detected, where the drug may be delivered in various ways as described below.

2. Detection of Ischemia

In order to detect whether the patient is experiencing cardiac ischemia, the controller is programmed to analyze the recorded electrogram of an evoked response to a pace or of an intrinsic contraction and look for morphological and temporal markers of a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes continuously depolarized or by an ischemic region that remains abnormally depolarized during all or part of the cardiac cycle. A current of injury results in an abnormal change in morphology and timing of the electrical potentials measured by either a surface electrocardiogram or an intracardiac electrogram. In the normal heart there is a period during the cardiac cycle, at the start of the contraction phase, when the cells in the ventricle are essentially isopotential. Electrocardiographically this segment occurs between the end of the QRS complex and the T wave and is referred to as the ST segment. The spatio-temporal dispersion of repolarization starts the relaxation phase of the heart and results in the T-wave on the electrocardiogram. In ischemic tissue, the individual cellular potentials are blunted resulting in a spatial and temporal dispersion of membrane potential during periods when the normal heart is isopotential. This results in the current of injury which is reflected on the electrocardiogram as a positive or negative shift, depending on the location of the ischemic or infarcted region. Traditionally, however, it is the ST segment that is regarded as shifted when an abnormal current of injury is detected by an electrogram or electrocardiogram. A current of injury produced by an ischemic region that does not last for the entire cardiac cycle may only shift part of the ST segment, resulting in an abnormal slope of the segment.

As aforesaid, an electrogram of an evoked response to a pace can be recorded and used to detect cardiac ischemia in accordance with the invention. An evoked response is the wave of depolarization that results from a pacing pulse and, since it evidences that the paced chamber has responded appropriately and contracted, it can also be used to verify that the pace has achieved capture of the heart. Sensing channels in a pacemaker that provide senses for controlling pacing are commonly rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channel is used for both sensing intrinsic activity to control pacing and for sensing an evoked response, a period for sensing an evoked response should preferably be defined that supercedes any normal refractory period of the sensing channel.

An ischemia detection-sensing channel for recording an electrogram can be a sensing channel used for other purposes or can be a sensing channel dedicated to sensing electrograms for ischemia detection. In order to detect ischemic changes in an electrogram, it is preferable to record the electrogram with a unipolar electrode that "sees" a larger volume of the myocardium as a wave of electrical activity spreads than a bipolar electrode. In the embodiment illustrated in FIG. 1A, the atrial and ventricular sensing pacing channels utilize bipolar electrodes, and a dedicated ischemia detection sensing channel is provided with a unipolar electrode. Alternate embodiments may employ unipolar electrodes in the atrial and/or sensing/pacing channels, in which case unipolar sensing of an electrogram for ischemia detection may be performed with those channels instead of a dedicated channel.

Figure 2:
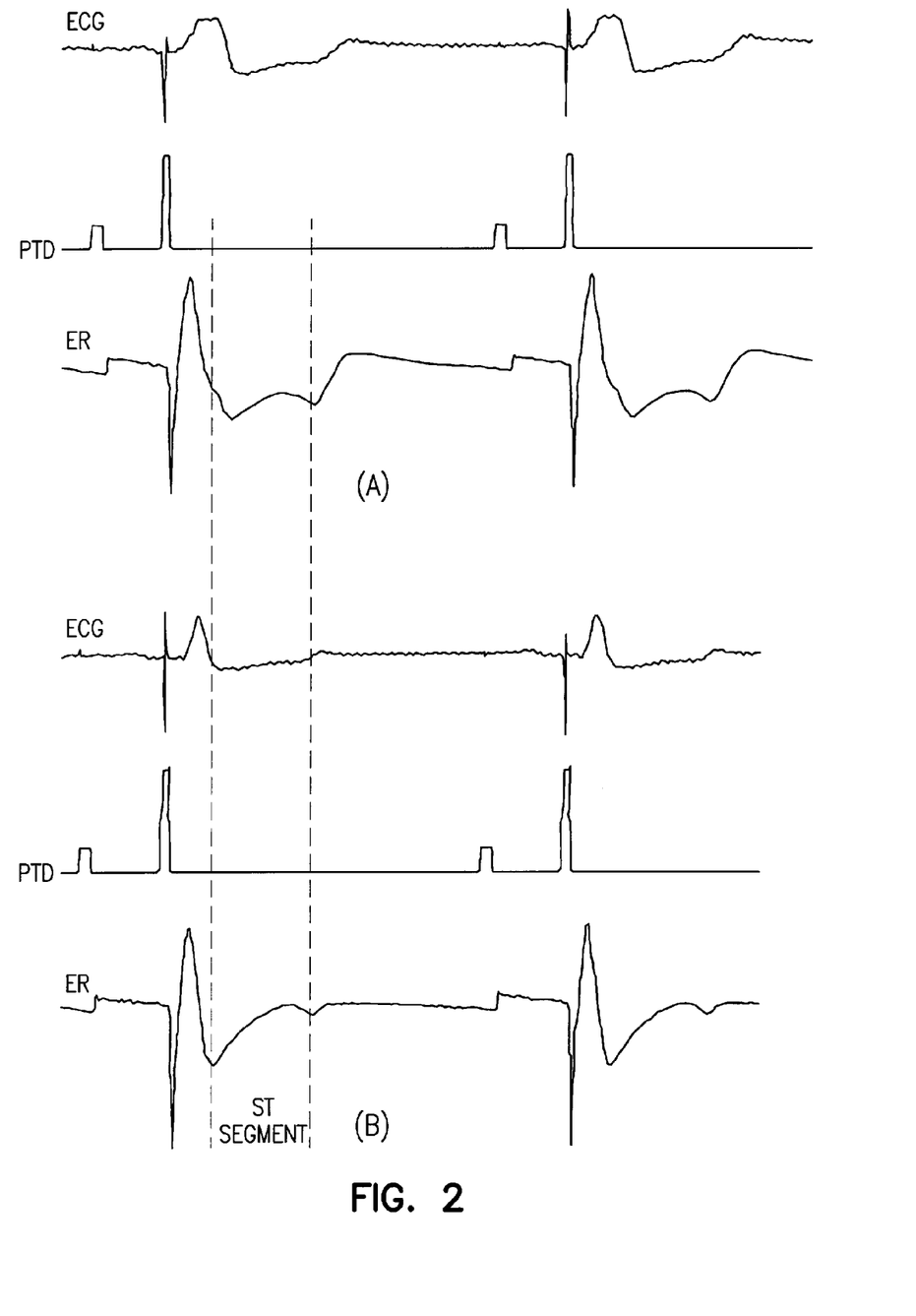
FIG. 2 illustrates ischemic changes in a recorded electrogram.

A change in an electrogram indicative of ischemia is detected by recording the electrogram and comparing it with a reference electrogram, which may either be a complete recorded electrogram or particular reference values representative of an electrogram. Because certain patients may exhibit a current of injury in a reference electrogram as a the result of a subclinical ischemic condition (e.g., coronary artery disease) or as the result of an inherited or acquired disease (e.g., Brugada Syndrome), the controller is programmed to detect ischemia by looking for an increased current of injury in the recorded electrogram as compared with the reference electrogram, where the latter may or may not exhibit a current of injury. FIG. 2 shows examples of evoked response data for two cases labeled A and B, where A is the baseline reference and B is during an acute ischemic episode. A surface electrocardiogram labeled ECG, a pacing timing diagram labeled PTD, and an electrogram labeled ER are illustrated for each case. The ST segment of the electrogram for case B is seen to have a different amplitude and slope as compared with the amplitude and slope of the ST segment of the electrogram for case A. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

If a change in a recorded electrogram indicative of ischemia is detected, the device controller may be programmed to deliver a thrombolytic agent or other cardiac drug by writing a command to the drug delivery interface. Because of the risks attendant with administering cardiac drugs in an uncontrolled setting, the drug should only be delivered when the ischemia is severe enough to warrant it. The methods for detecting ischemia in a recorded electrogram discussed above are advantageous in this regard because the degree of ischemia can be quantified as, for example, the extent of correlation between the recorded and reference electrograms, measured amplitude or slope of an ST segment, or result of integrating the ST segment. The quantitative measure of ischemia necessary before the device delivers a drug dose can then be adjusted by a clinician until the drug delivery criteria has the desired specificity and sensitivity.

A detected ischemic change may also be logged as a clinically significant event in the device's memory. The event log and/or the recorded electrogram exhibiting the ischemia may then be later downloaded to a clinician for analysis via an external programmer. The clinician is then able to use this information in making subsequent treatment decisions.

3. Additional Criteria for Drug Delivery

As aforesaid, delivery of certain cardiac drugs can present risks to the patient. It is therefore desirable for the criteria used in detecting ischemic events that initiate therapy to be as specific as possible in order to minimize the possibility of a false-positive detection causing unwarranted drug delivery. As noted above, the present invention allows the degree of ischemia detected from an electrogram to be quantified so that the ischemia detection criterion can be adjusted to the desired specificity and sensitivity. Another way of increasing the specificity of event detection for drug delivery is to use additional criteria based on other measurable physiological variables which correlate either with cardiac ischemia or with the need for drug delivery during such events such as heart rate variability, minute ventilation, and activity level. Drug delivery can then be initiated if ischemic changes are detected in the electrogram and if one or more of the additional criteria are also met.

Cardiac ischemia causes metabolic stress that the body responds to with increased activity of the sympathetic nervous system. Among the indicia of such increased sympathetic activity is the frequency spectrum of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. Additional specificity for initiating drug delivery may thus be provided by monitoring the LF/HF ratio and initiating drug therapy only if it exceeds a specified threshold value. The predetermined threshold value may be fixed or may be determined by the device based upon previous measurements. For example, the LF/HF threshold may be set to 50% of the maximum computed LF/HF ratio value during the previous day.

Figure 1B:
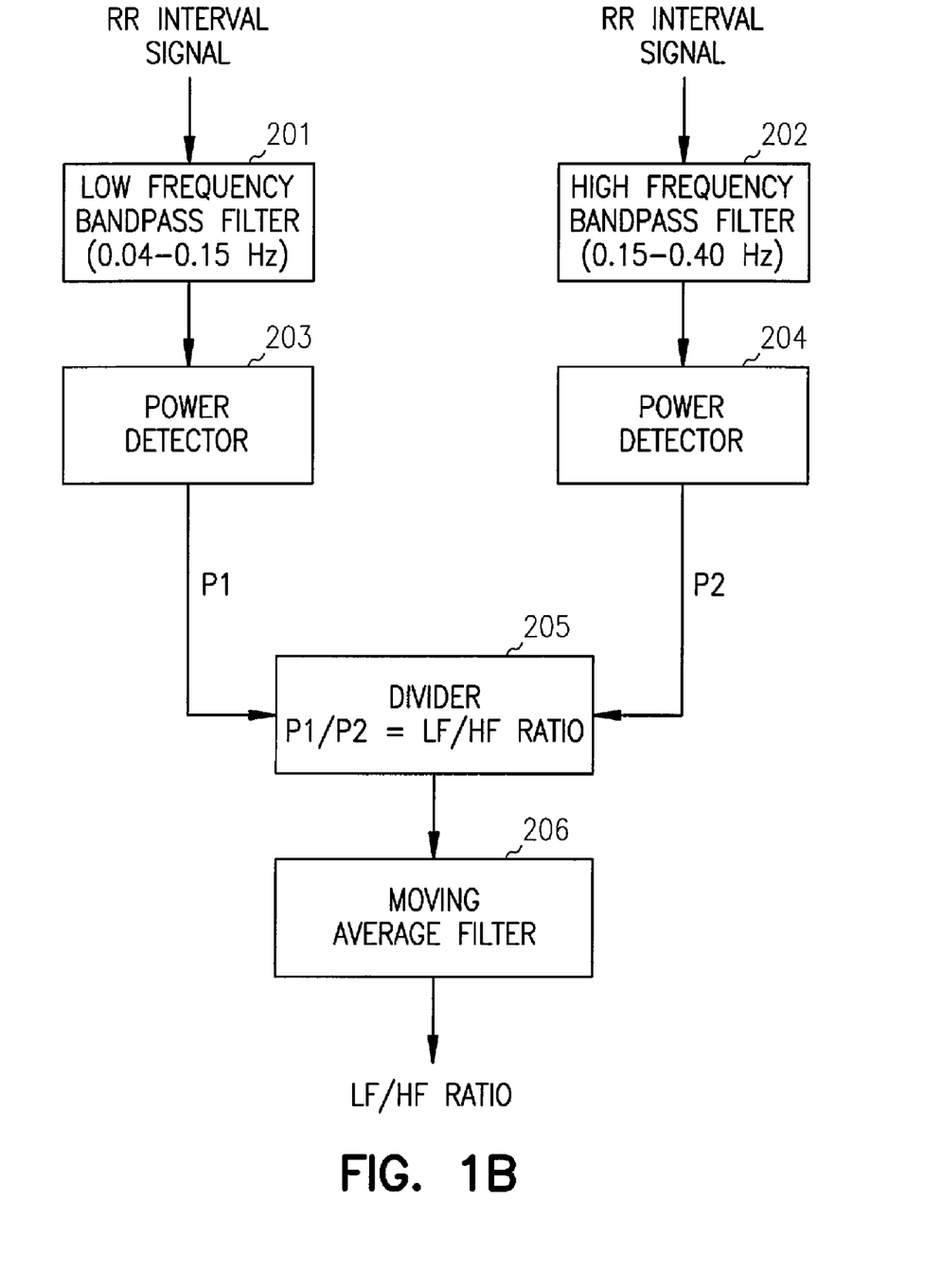
FIG. 1B is a block diagram of components for analyzing the frequency spectrum of intervals between heartbeats.

A cardiac rhythm management device can be programmed to determine the LF/HF ratio by analyzing data received from its ventricular sensing channels. The intervals between successive ventricular senses, referred to as RR intervals, can be measured and collected for a period of time or a specified number of beats. In order to derive a signal representing heart rate variability during a sinus rhythm, ectopic ventricular beats (i.e., premature ventricular contractions or PVCs) can be detected by monitoring whether a P wave precedes each R wave, with the RR intervals before and after the PVC changed to an interpolated or otherwise filtered value. The resulting series of RR interval values is then stored as a discrete signal. The signal can be used directly as indexed by heartbeat such that each value of the signal represents an RR interval for a particular heartbeat. Preferably, however, the signal is resampled at a specified sampling frequency in order to equalize the time intervals between signal values and thus convert the signal into a discrete time signal, where the sampling frequency is selected to meet the Nyquist criterion with respect to the frequencies of interest. In any case, the RR interval signal can then be analyzed to determine its energies in the high and low frequency bands as described above. Spectral analysis of an RR interval signal can be performed directly in the frequency domain using discrete Fourier transform or autoregression techniques. Frequency domain analysis is computationally intensive, however, and may not be practical in an implantable device. A time-domain technique for determining the high and low frequency components of the signal is therefore preferably used. FIG. 1B illustrates the functional components of an exemplary system for doing this that can be implemented as code executed by the controller and/or dedicated hardware components. The RR interval signal obtained as described above is input to both a low band digital filter 201 and a high band digital filter 202. The low band filter 201 is a bandpass filter with a passband corresponding to the LF band (e.g., 0.04 to 0.15 Hz), while the high band filter 202 is a bandpass filter with a passband corresponding to the HF band (e.g., 0.15 to 0.40 Hz). The outputs of filters 201 and 202 are then input to power detectors 203 and 204, respectively, in order to derive signals proportional to the power of the RR interval signal in each of the LF and HF bands. Power detection may be performed, for example, by squaring the amplitude of the signal and integrating over a specified average time. The output of power detector 203 is thus a signal P1 that represents the power of the RR interval signal in the LF band, and the output of power detector 204 is a signal P2 representing the power in the HF band. The signals P1 and P2 are next input to a divider 205 that computes the quantity S1/S2 which equals the LF/HF ratio. The LF/HF ratio is then input to a moving average filter 206 that computes an average value for the ratio over a specified period (e.g., 5 minutes). An updated LF/HF ratio may be computed in this manner on a beat-to-beat basis.

Another useful physiological variable that correlates with cardiac ischemia is the respiratory rate. Patients suffering a heart attack subjectively experience shortness of breath and attempt to compensate by increasing their respiratory rate. The sensor normally used for measuring minute ventilation can also be used to measure respiratory rate, with drug delivery then being initiated only if the measured respiratory rate is above a specified threshold value.

Another variable that may be useful in determining if drug therapy for treating cardiac ischemia is warranted is the patient's activity level as measured by an accelerometer. Cardiac ischemia may occur while the patient is either active or at rest. Exertional angina, for example, occurs when a patient experiences cardiac pain from cardiac ischemia due to an increased exertion level. If the angina is stable, meaning that the pain disappears when the patient's exertion level returns to a resting value, the situation is not ordinarily considered emergent. It therefore may not be desirable for an implantable device to automatically deliver a drug upon detection of cardiac ischemia in such a situation. Accordingly, the device may be programmed to deliver drug therapy only when cardiac ischemia is detected from the electrogram and a resting activity level is detected by the accelerometer as indicated by the measured activity level being below a specified threshold value.

4. Delivery of Cardiac Drugs

Figure 3:
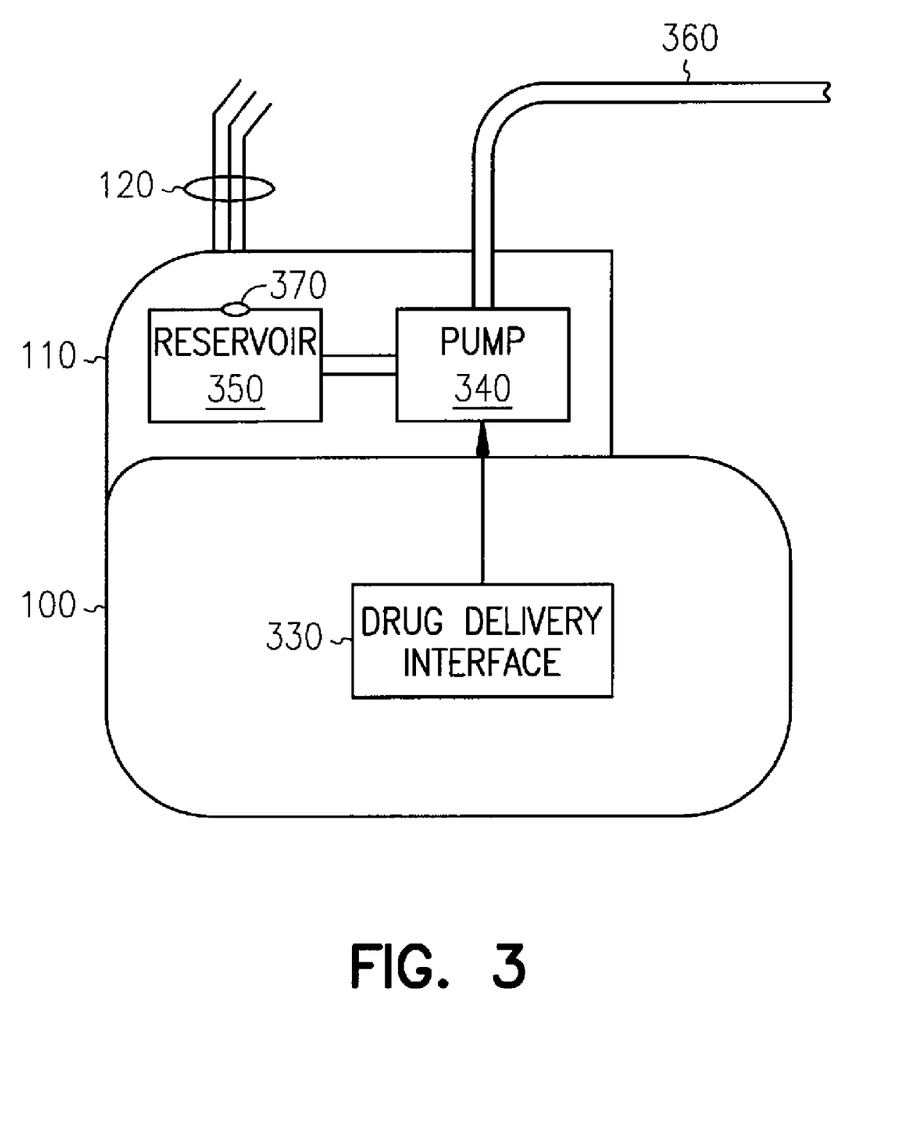
FIG. 3 shows an exemplary drug delivery drug delivery apparatus utilizing an intravenous catheter.
Figure 4A:
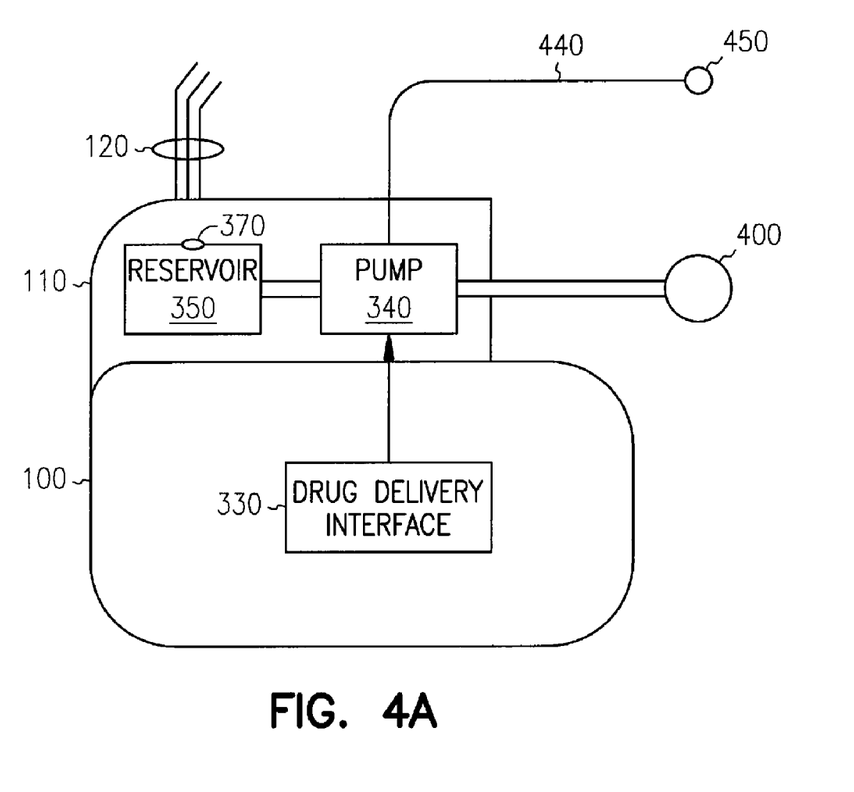
FIGS. 4A-B show an exemplary drug delivery apparatus utilizing patch electrodes.
Figure 4B:
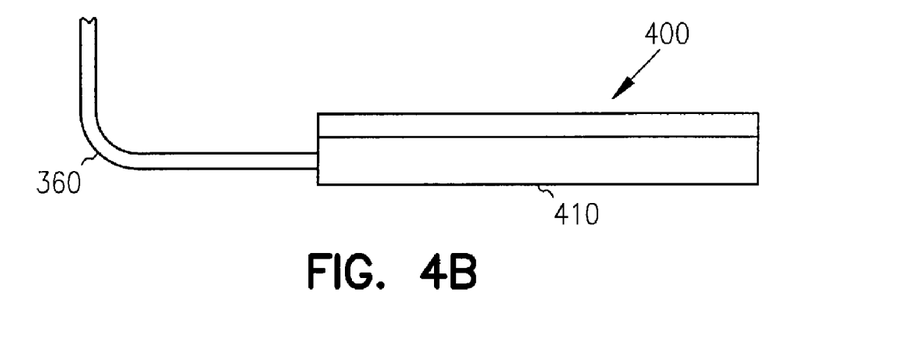

Once the controller 10 detects an ischemic change in an electrogram warranting administration of a cardiac drug, a command is issued to the drug delivery interface 330. The drug delivery interface then actuates the drug delivery apparatus incorporated into the device, examples of which are illustrated in FIGS. 3 and 4A-B. In FIG. 3, a cardiac rhythm management device is depicted which includes a metallic housing 100 and a header portion 110. Leads 120 used for sensing and/or pacing enter the header 110 and then pass into the interior of the housing via feedthrough assemblies that maintain the hermetic sealing of the housing. A pump 340 and a drug reservoir 350 located within the header 10 communicate with a catheter 360. The drug delivery interface 330 within the housing communicates with the pump 340 by control wires that pass into the header through a feedthrough. Upon actuation by the drug delivery interface 330, the pump 340 pumps a quantity of drug from a reservoir 350 into the lumen of a catheter 360. By locating the pump and drug reservoir in the header, an external port 370 can be provided through which a quantity of drug can be injected in order to replenish the reservoir.

The catheter 360 may be passed into patient intravenously along with the sensing/pacing leads so that the pumped quantity of drug egresses out the distal end of the catheter and into the patient's bloodstream. The distal end of the catheter may also be disposed at a cardiac location. In modifications to this embodiment, the catheter may incorporate lead wires and electrodes for facilitating the drug delivery such as by iontophoresis, electroporation, electrorepulsion, or electro-osmosis. The current to the electrodes in that case is then actuated by the drug delivery interface in coordination with operation of the pump.

FIGS. 4A and 4B show an alternative embodiment where the distal end of the catheter 360 is attached to a patch electrode 400 for iontophoretic drug delivery. The patch electrode may, for example, be disposed at a subcutaneous location on the patient's chest or abdomen. The patch electrode 400 has a drug reservoir 410 into which a quantity of drug is pumped by the pump 340 during a drug delivery operation. A separate lead 440 with a patch electrode 450 is also provided so that a voltage can be impressed across the patch electrodes 400 and 450 during drug delivery. The impressed voltage then causes migration of charged drug molecules from the reservoir and into the body tissues. In an alternative embodiment, the patch electrodes 400 and 450 are mounted on the device housing 100. External drug delivery means may also be used by the device for drug delivery in response to ischemia. Examples of external drug delivery apparatus are disclosed in U.S. Pat. No. 6,361,522, assigned to the assignee of the present application and hereby incorporated by reference.

Finally, the device may be programmed to deliver drugs upon detection of conditions other than ischemia, which may be beneficial for certain patients. For example, an anti-platelet drug or heparin may be administered by the device when atrial fibrillation is detected.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable cardiac device, comprising:
a sense amplifier for receiving an electrogram signal from an electrode;
circuitry for storing a reference electrogram;
circuitry configured to record an electrogram received by the sense amplifier and to detect a change in the recorded electrogram indicative of cardiac ischemia by comparing the recorded electrogram with the reference electrogram, wherein the circuitry is further configured to perform the comparison by passing the recorded electrogram through a matched filter that cross-correlates the recorded electrogram with the reference electrogram;
a minute ventilation sensor for measuring a patient's respiratory rate;
a drug delivery apparatus for delivering a quantity of a cardiac drug; and,
circuitry configured to actuate the drug delivery apparatus and further configured to initiate drug delivery only if both of the following conditions are met: 1) cardiac ischemia is detected from the recorded electrogram, and 2) the measured respiratory rate is above a specified threshold.

2. The device of claim 1 wherein the drug delivery apparatus includes a catheter.

3. The device of claim 2 wherein the drug delivery apparatus includes a drug reservoir and a pump for pumping a quantity of drug into a lumen of the catheter.

4. The device of claim 3 further comprising a header and wherein the pump and drug reservoir are located in the header of the device.

5. The device of claim 1 wherein the circuitry configured to detect a change in the recorded electrogram quantifies the degree of ischemia and further wherein the circuitry configured to cause delivery of a cardiac drug does so only when the degree of ischemia is above a programmable threshold value.

6. The device of claim 1 wherein the cardiac drug is a thrombolytic drug.

7. The device of claim 1 further comprising an accelerometer for measuring a patient's activity level and wherein the circuitry configured to actuate the drug delivery apparatus does so only if the measured activity level is below a specified threshold value.

8. The device of claim 1 further comprising a pulse generator for delivering pacing pulses and wherein the circuitry configured to record an electrogram is configured to record an evoked response to a pacing pulse.

9. A method for operating a cardiac device implanted in a patient, comprising:
sensing intrinsic cardiac activity;
recording an electrogram from the sensed cardiac activity;
detecting cardiac ischemia by comparing the recorded electrogram with a reference electrogram, wherein the comparison is performed by passing the recorded electrogram through a matched filter that cross-correlates the recorded electrogram with the reference electrogram;
measuring the patient's respiratory rate; and,
delivering a cardiac drug and initiating cardiac drug delivery only if both of the following conditions are met: 1) cardiac ischemia is detected from the recorded electrogram, and 2) the measured respiratory rate is above a specified threshold.

10. The method of claim 9 further comprising delivering the cardiac drug through a catheter.

11. The method of claim 10 further comprising pumping the cardiac drug from a reservoir.

12. The method of claim 11 wherein the reservoir is located in a header of the cardiac device.

13. The method of claim 9 further comprising quantifying the degree of ischemia and delivering a cardiac drug only when the degree of ischemia is above a programmable threshold value.

14. The method of claim 9 wherein the cardiac drug is a thrombolytic drug.

15. The method of claim 9 further comprising:
measuring the patient's activity level; and,
delivering a cardiac drug only when an ischemic condition is detected from the recorded electrogram and the measured activity level is below a specified threshold value.

16. The method of claim 9 wherein the recorded electrogram is an evoked response to a pace.

* * * * *